United States Patent
Ketcham et al.

(10) Patent No.: US 9,885,640 B2
(45) Date of Patent: Feb. 6, 2018

(54) PARTICLE IMPACTOR WITH SELECTIVE HEIGHT ADJUSTMENT

(71) Applicant: Particle Measuring Systems, Inc., Boulder, CO (US)

(72) Inventors: Cliff Ketcham, Golden, CO (US); Paul B. Hartigan, Longmont, CO (US); Chandrasekar Lakshmanan, Karnatatak (IN)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 127 days.

(21) Appl. No.: 14/645,753

(22) Filed: Mar. 12, 2015

(65) Prior Publication Data

US 2015/0260617 A1 Sep. 17, 2015

Related U.S. Application Data

(60) Provisional application No. 61/953,306, filed on Mar. 14, 2014.

(51) Int. Cl.
| | | |
|---|---|---|
| *G01N 1/22* | (2006.01) | |
| *G01N 15/02* | (2006.01) | |
| *G01N 15/00* | (2006.01) | |

(52) U.S. Cl.
CPC ....... *G01N 1/2208* (2013.01); *G01N 15/0255* (2013.01); *G01N 2015/0065* (2013.01); *G01N 2015/0261* (2013.01)

(58) Field of Classification Search
CPC ......... G01N 1/2208; G01N 2015/0261; G01N 15/0255; G01N 1/2202; G01N 2001/2223

(Continued)

(56) References Cited

U.S. PATENT DOCUMENTS 3,972,226 A * 8/1976 Rountree ............. G01N 1/2202
73/28.05
4,640,140 A * 2/1987 Burghoffer ......... G01N 15/0255
73/863.22

(Continued)

OTHER PUBLICATIONS

Biswas et al. (1984) "High-velocity inertial impactors," *Environ. Sci. Technol.* 18(8):611-616.

(Continued)

*Primary Examiner* — Eric S McCall
*Assistant Examiner* — Mohammed E Keramet-Amircola
(74) *Attorney, Agent, or Firm* — Lathrop Gage LLP

(57) ABSTRACT

Provided are impactors for detecting biologics having an adjustable separation distance between an impact surface and the intake aperture, including the exit of the intake aperture. The impactor has a sampling head having at least one intake aperture and an exit, an impactor base comprising an impact surface, wherein the impact surface opposibly faces the sampling head exit and is separated from the exit by a separation distance. The separation distance is continuously adjustable between a minimum separation distance and a maximum separation distance and can accommodate impact surfaces having different heights by positioning the impact surface, irrespective of height of the impact surface, at an optimal separation distance from the sample intake aperture, such as by a rotation-type mechanism with a change in distance indication provided to a user by a separation distance step indicator.

27 Claims, 7 Drawing Sheets

(58) Field of Classification Search
USPC ...................................................... 73/863.22
See application file for complete search history.

(56) References Cited

U.S. PATENT DOCUMENTS

| | | | | |
|---|---|---|---|---|
| 4,827,779 A * | 5/1989 | Marple | ................ | G01N 1/2205 |
| | | | | 73/863.22 |
| 5,693,895 A * | 12/1997 | Baxter | ................ | G01N 1/2208 |
| | | | | 73/28.05 |
| 5,831,182 A * | 11/1998 | Swenson | ............... | G01N 1/2208 |
| | | | | 73/863.22 |
| 6,435,043 B1 * | 8/2002 | Ferguson | ............. | G01N 1/2208 |
| | | | | 73/863.22 |
| 6,685,759 B2 * | 2/2004 | Dahlin | .................... | B04C 5/185 |
| | | | | 55/464 |
| 7,799,567 B1 * | 9/2010 | Call | ......................... | B07B 7/00 |
| | | | | 436/174 |
| 2001/0029793 A1 | 10/2001 | Moler et al. | | |
| 2002/0066321 A1 * | 6/2002 | Lagraff | ................ | G01N 1/2208 |
| | | | | 73/863.22 |
| 2003/0008341 A1 * | 1/2003 | Spurrell | ............... | G01N 1/2205 |
| | | | | 435/34 |
| 2004/0069047 A1 | 4/2004 | Coyle et al. | | |
| 2007/0269849 A1 * | 11/2007 | Bridenne | ............. | G01N 1/2202 |
| | | | | 435/30 |
| 2008/0087108 A1 | 4/2008 | Kreikebaum et al. | | |
| 2009/0078062 A1 * | 3/2009 | Maheshwari | ........ | G01N 1/2208 |
| | | | | 73/863.22 |
| 2010/0212436 A1 * | 8/2010 | Swenson | ............... | G01N 1/2208 |
| | | | | 73/863.22 |
| 2010/0288057 A1 * | 11/2010 | Witham | ................ | B01D 45/08 |
| | | | | 73/863.22 |
| 2011/0167931 A1 * | 7/2011 | Vellutato, Jr. | ........ | G01N 33/497 |
| | | | | 73/863.11 |
| 2012/0247233 A1 * | 10/2012 | Maheshwari | ........ | G01N 1/2208 |
| | | | | 73/863.22 |
| 2013/0084597 A1 * | 4/2013 | Rebe | ....................... | C12Q 1/04 |
| | | | | 435/34 |

OTHER PUBLICATIONS

International Search Report with Written Opinion corresponding to International Patent Application No. PCT/US2015/020090, dated Jun. 12, 2015.

* cited by examiner

PARTICLE IMPACTOR WITH SELECTIVE HEIGHT ADJUSTMENT

CROSS-REFERENCE TO RELATED APPLICATIONS

This application claims the benefit of priority from U.S. Provisional Patent Application No. 61/953,306 filed Mar. 14, 2014, which is hereby incorporated by reference in its entirety to the extent not inconsistent herewith.

BACKGROUND OF INVENTION

The invention is in the field of particle sampling, collection and analysis. The invention relates generally to devices and methods for sampling and characterizing particles in fluids include air and process chemicals (e.g., gases and liquids) for applications including the evaluation of contaminants in a range of cleanroom and manufacturing environments. More specifically, provided are impactors having a spatial adjustment to position an impact surface at an optimal separation distance from an intake aperture exit, independent of the height of the impact surface or the type of container in which the impact surface is located.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the Food and Drug Administration (FDA).

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones and liquid particle counters are used to optically measure particle contamination levels in process fluids. Where microbiological particles are a particular concern, such as in the pharmaceutical industry, not only is quantification of the number of airborne particles important, but evaluating the viability and identity of microbiological particles is also important. ISO 14698-1 and 14698-2 provide standards for evaluation of cleanroom and clean zone environments for biocontaminants.

Collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each single stage of an inertial impactor operates on the principle that particles suspended in air can be collected by forcing a dramatic change in the direction of the particle containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.*, 1984, 18(8), 611-616).

In many cleanroom environments, retrieving size information from a particle impactor is not necessary. In this case, a single stage active air sampling impactor system is sufficient to collect biological particle concentrations subject to subsequent detection and analysis. In an impactor-based active air sampler used for collection of biological particles, the impact/collection surface commonly comprises a growth medium, such as an agar plate, as would be used with other biological particle collection techniques. After the particles are collected onto the growth media surface, the media is incubated to allow the biological particles to reproduce. Once the colonies reach a large enough size, they can be identified and characterized, for example using microscopic imaging, fluorescence, staining or other techniques, or simply counted visually by eye or by image analysis techniques.

For these types of biological particle collection and analysis techniques, various operational aspects are important to ensure efficient collection, detection and analysis. For example, the collection efficiency is of critical importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon impact with the growth medium, such that the collected particles do not replicate during the incubation process and, therefore, cannot be subsequently identified.

There remains a need in the art for particle collection systems capable of achieving efficient sampling of biological particles. For example, particle collection systems are needed for cleanroom and manufacturing applications that provide high particle collection efficiencies while maintaining the viabilities of collected bioparticles.

SUMMARY OF THE INVENTION

Provided herein are methods and devices for achieving an optimal separation distance of an impact surface from an exit of an intake aperture.

In an embodiment, provided herein are impactors having a continuously adjustable separation distance between an impactor surface and the exit of an air inlet that is opposibly positioned to the impactor surface so as to facilitate positioning of the impact surface at an optimal separation distance from the exit of the air inlet. This provides a number of functional benefits, including being able to use an impactor with a wide range of biological growth media and containers, wherein change in the depth of the biological growth media is accommodated herein by the adjustable separation distance. Containers and corresponding growth media that may be deeper or higher may be accommodated as well as relatively thinner containers and corresponding growth media to achieve an optimal separation distance irrespective of the container and growth media depth.

In an embodiment, the impactor comprises a sampling head having at least one intake aperture and an exit and an impactor base comprising an impact surface. The impactor base may have a surface that supports, holds or confines an impaction media or media container which hold or confines an impaction media. The impaction media defines in turn an impact surface. The impaction media may be a growth media. The impact surface opposibly faces the sampling head exit and is separated from the exit by a separation distance. The separation distance is continuously adjustable between a minimum separation distance and a maximum separation distance. "Continuously adjustable" is used broadly herein to refer to distances that can be adjusted to ensure an optimum separation distance is achieved even for impact surfaces having different heights. For impact surfaces having a large height, the continuously adjustable allows the impact surface to be backed off from the aperture exit to attain the optimum separation distance. For impact surfaces having a relatively small height, the continuously adjustable allows the impact surface to be brought toward the aperture exit to attain the optimum separation distance, wherein the optimum separation distance is the same for both impact surface heights. As flow conditions change, the optimum separation distance may change to ensure efficient capture of biological particles in the airstream without adversely damaging the biological particles upon impact with the impact surface. Any of the adjustment plates provided herein may be characterized as a "rotatable adjustment plate" in that the continuously adjustable separation adjustment may be achieved by rotation of the adjustment relative to another component of the impactor, such as a base plate of the impactor base.

Another advantageous aspect of the devices and methods provided herein is the ability to easily and reliably step through the separation distances in an indexed or ratcheting-type manner. For example, while the separation distances are continuously adjustable, it is helpful to a user to have some indication as to the increment by which the separation distance changes. Any of the impactors and methods provided herein may provide an indication of such step change in separation distance by a separation distance step indicator operably connected to the base plate or the adjustment plate to indicate a change in the separation distance for a given rotation of the adjustment plate. The invention is compatible with a wide range of components to facilitate such changes, including a paired protrusion element and indent that provide reliable, but reversible, setting of a separation distance.

In an aspect, the impactor base further comprises an adjustment plate rotably connected to a base plate, wherein the adjustment plate and the base plate rotably move relative to each other to provide the continuously adjustable separation distance. Any number of relative motions may be employed so that the relative motion translates to a change in the separation distance so as to accommodate different impact surface heights, for example. For example, an up/down motion may be used to directly correspond to changes in separation distance. Another example is rotation, analogous to a threaded screw and nut configuration, wherein rotation of the screw provides a change in separation distance. Although the systems and methods provided herein refer to continuous adjustability, there may be preferred set-points corresponding to discrete changes in separation distance. Such set-points assist with achieving a desired positioning of the impact surface and helps ensure the desired position is maintained during sampling. Accordingly, any of the methods and devices provided herein may further comprise a plurality of set-points that provide a desired separation distance that is not susceptible to accidental change. The set-points may be by a plurality of indents and a protrusion element configured to interact with the indents, as described hereinbelow. Other mechanisms may be used as desired, such as other shapes, magnetic forces, or friction enhancing elements. As described, this aspect is generally referred herein as a separation distance step indicator. The separation distance step indicator may be operably connected to the base plate, the adjustment plate, or both, to indicate a change in the separation distance for a given rotation of the adjustment plate.

In an aspect, the adjustment plate rotates relative to the base plate, wherein rotation of the adjustment plate relative to the base plate provides the continuously adjustable separation distance. In an alternative aspect, the adjustment plate is connected to the base plate by a protrusion element that is a set-screw that controls relative vertical movement between the adjustment plate and the base plate.

In an aspect, the adjustment plate comprises a threaded collar and the base plate comprises a threaded opening, wherein the threaded collar and threaded opening form paired internal-external threads to provide the continuously adjustable separation distance by rotation of the threaded collar relative to the threaded opening.

Any of the impactors and related methods described herein may relate to a separation distance that corresponds to an optimal separation distance.

In an embodiment, the optimal separation distance is about twice a characteristic dimension of an opening size of the sampling head exit, such as an effective diameter of the cross-sectional opening or a width. In an aspect, the optimal separation distance is greater than or equal to 0.1 mm and less than or equal to 5 mm, or greater than or equal to 0.4 mm and less than or equal to 0.8 mm. In an aspect, the optimal separation distance is greater than or equal to an opening size of the sampling head exit and less than or equal to about three times the width of the intake aperture exit. Examples of an opening size of the sampling head include the aperture inlet width or the aperture exit width.

In an embodiment, any of the impactors have a minimum separation that is selected from a range that is greater than 0 and less than 0.2 mm and a maximum separation distance greater than the minimum separation distance and selected from a range that is greater than 0.1 mm and less than or equal to 5 mm. In this manner, the systems may accommodate any reasonable thickness associated with an impact surface as well as containers of any reasonable height that confine the impact surface.

Any of the impactors provided herein may further comprising a protrusion element connected to the base plate and a plurality of indents formed on a surface of the adjustment plate, wherein the protrusion element is configured to mate with each of the plurality of indents. This may assist with positioning the impactor surface relative to the base plate, thereby ensuring a desired separation is achieved. For example, the plurality of indents may be equally spaced apart from each other by an indent separation distance, wherein a change in mating of the protrusion element from a first indent to an adjacent indent corresponds to a change in the separation distance. In an aspect, the indent separation distance is selected to provide the change in the separation distance that is greater than or equal to 0.05 mm and less than or equal to 0.5 mm. In this fashion, the separation distance may be consecutively changed in increments of the indent separation distance. For applications where the container-to-container variability of impact surface height is relatively small, the indent separation distance may be correspondingly small, such as about 0.05 mm to 0.1 mm. For applications where the container-to-container variability of impact surface height is relatively high, the indent separation distance may be relatively larger.

There are any number of configurations that provide height adjustability between the impact surface and the base plate. For example, the adjustment plate may comprise a rotatable adjustment plate having a collar and the base plate comprises a threaded opening, or vice versa. The threaded collar and threaded opening form paired internal-external threads to provide the continuously adjustable separation distance by rotation of the threaded collar relative to the threaded opening. The plurality of indents are concentrically positioned around the collar and configured to receive the protrusion element, so that rotation of the adjustable plate from a first indent to a spatially adjacent second indent corresponds to the change in separation distance.

Mating of the protrusion element with an indent is indicated by an audible mechanically-generated sound by physical interaction between the protrusion element and the indent.

In an embodiment, the protrusion element comprises a spherically shaped outer surface and the indent is shaped to receive at least a portion of the spherically shaped outer surface.

In an aspect, any of the impactors provided herein further comprise a visualization indicator connected to the impactor base for positioning the impactor surface at a separation distance corresponding to a desired separation distance. In an embodiment, the impactor of comprises a plurality of visualization indicators, such as a first visualization indicator and a second visualization indicator, wherein the first and second visualization indicators are opposibly positioned with respect to each other, wherein the impact surface is positioned between the first and the second visualization indicators.

In an embodiment, the plurality of visualization indicators secure the sampling head to the impactor base. In this embodiment, the visualization indictors may be shaped to clip or fasten to an outside wall of a container in which the impact surface is confined, or may interact with the container under tension so as to reliably position and secure the container. In this manner, the container is both reliably secured to a support surface and facilities ready removal of the impact surface from the impactor and loading of the impactor with a new impact surface confined in a new container.

In an aspect, the impactor further comprises a container in which the impact surface is positioned, wherein the container has a side wall that constrains the impact surface and at least a portion of the side wall is optically transparent for visual alignment of the visualization indicator with a top surface of the impact surface. For aspects where the side wall is not optically transparent, the impact surface may correspond to the top-most portion of the side wall.

The impact surface may comprise a top surface of a growth medium, and the top surface of the growth medium is aligned with the plurality of visualization indicators. The impact surface may be constrained within a container having a sidewall top and the impact surface top surface is substantially coincident with the container sidewall top.

In an embodiment, any of the impactors described herein have an impact surface comprising a top surface of a biological growth medium. The biological growth medium may comprise agar, a liquid growth media, or a broth, so long as the biological growth media is capable of supporting growth of a biological particle, such as bacteria. In an aspect, the biological growth media is confined within a growth media container.

In an aspect, the impactor base further comprises a rotatable adjustment plate and a base plate that supports the rotatable adjustment plate. The rotatable adjustment plate comprises a threaded collar and the base plate comprises a threaded opening and rotation of the threaded collar relative to the threaded opening provides the continuously adjustable separation distance. The threaded collar is connected to a bottom surface of the rotatable adjustment plate, and the growth media container is supported by a top surface of the rotatable adjustment plate.

One example of a growth media container is a cell culture dish such as a petri dish or other shallow dish capable of supporting a growth media for culturing biological particles, including bacteria.

In an embodiment, the impactor base is adjusted to achieve an optimal separation distance that accommodates container-to-container variation in a growth media depth of the biological growth media confined within the growth media container.

The growth media container in the impactor may be removable and replaceable.

In an aspect, the depth of the growth media within the growth media container is different for a replacement growth media container, and the continuously adjustable separation distance is selected so as to maintain an optimal separation distance for the replacement growth media container.

In an aspect, the sampling head comprises a plurality of openings, each opening having an inlet and an outlet.

Also provided herein are methods for detecting biological particles with an impactor, including any of the impactors described herein. In an aspect, the method comprises the steps of providing a biological growth media in a media container, the biological growth media having a top surface that corresponds to an impact surface; positioning the media container on a top surface of an adjustment plate, wherein the adjustment plate has a threaded collar connected to a bottom surface of the adjustment plate; rotatably connecting the adjustment plate to threaded opening on an impactor base; rotating the adjustment plate relative to the impactor base, thereby adjusting a separation distance between the impact surface and an exit of a sampling head of the impactor; aligning the impact surface with a plurality of visualization indicators, thereby adjusting the separation distance to correspond to an optimal separation distance; and flowing a sample fluid through the exit of the sampling head, wherein the optimal separation distance provides impaction of biological particles suspended in the sample fluid, thereby detecting the biological particles.

The method may further comprise rotating the adjustment plate relative to the impactor base, thereby continuously adjusting a separation distance between the impact surface and an exit of a sampling head of the impactor by an indexed separation distance. An adjusted separation distance corresponding to the indexed separation distance may be indicated to a user, wherein the indicating comprises a mechanically generated sound generated by a protrusion element moving into an indent with a rotation that provides a change in separation distance corresponding to the indexed separation distance. This provides additional information and control to a user trying to achieve a desired separation distance.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1A:
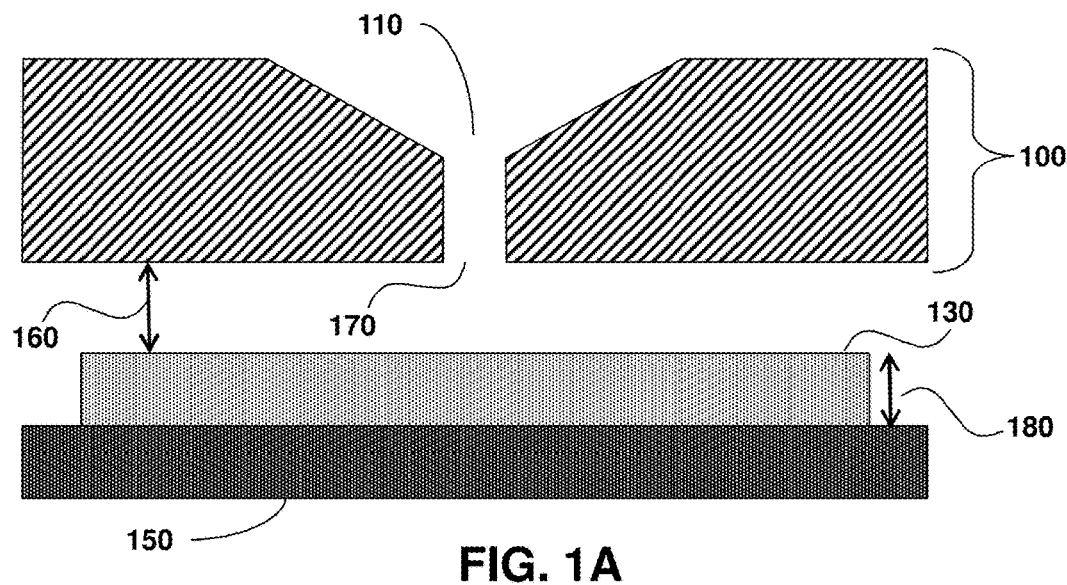
FIGS. 1A and 1B are schematic illustrations of fluid flow components for use with the impactor and corresponding fluid flow with respect to the impact surface.

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of less than 1-20 µm. Biological particles include viable biological particles capable of reproduction, for example, upon incubation with a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, particles comprising aggregates of material having a size greater than 50 nm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for example, via an incubation process involving a growth medium. Such growth is a useful indication of viability as well as for assisting in determining presence of biological particles by visual inspection. A sampler refers to a device for sampling particles.

Impactor refers to a device for sampling particles. In some embodiments, an impactor comprises a sample head including one or more intake apertures for sampling a fluid flow containing particles, whereby at least a portion of the particles are directed on to an impact surface for collection, such as the receiving surface of a growth medium (e.g., culture medium such as agar, broth, etc.) or a substrate such as a filter. Impactors of some embodiment, provide a change of direction of the flow after passage through the intake apertures, wherein particles having preselected characteristics (e.g., size greater than a threshold value) do not make the change in direct and, thus, are received by the impact surface. The threshold size value may be selected such as by varying the separation distance between the exit of the intake aperture and the impact surface and/or varying the flow rate through the intake aperture.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological, or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes. For laminar flow, flow direction corresponds to the direction of fluid flow streamlines.

"Optical communication" refers to an orientation of components such that the components are arranged in a manner that allows light or electromagnetic radiation to transfer between the components.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, a pressure sensor, a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area. In one embodiment the flow rate may correspond to an average fluid velocity calculated by the volumetric flow rate divided by the cross-sectional area of the fluid conduit in which flow occurs.

Laminar flow refers to a flow that is predictable, steady and not random, in contrast to turbulent flow, and such flows are useful in the devices and methods provided herein to better control impaction of particles satisfying a certain threshold size to improve detection characteristics. Laminar flow refers to flow situations where the ratio of inertial to viscous forces as defined by the Reynolds number ($Re=\rho VD/\mu$; $\rho$ is fluid density, V is average velocity, D is a size of the conduit in which the fluid flows, such as aperture dimension or separation distance, and $\mu$ is the fluid viscosity), is less than about 2000, less than about 1000, less than about 100, or less than about 1.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum or volume exerting zero force per unit area. Absolute pressure is distinguished from a "differential pressure" or "gauge pressure", which refers to a relative or difference in force exhibited per unit area in excess of or relative to a second pressure, such as an ambient pressure or atmospheric pressure.

"Optimal separation distance" refers to a distance between an impact surface and an aperture outlet that is selected so that substantially all particles above a threshold size will impact the impact surface, whereas particles below the threshold size are carried along with the fluid flow and exit without physically impacting the impact surface. "Substantially all particles" refers to at least 50%, at least 70%, or at least 90%, of particles above the threshold size impact the impactor surface. In the case of biological particles, at least 50%, at least 70%, or at least 90% of viable biological particles that impact the impact surface remain viable and capable of biological growth. In an aspect, the ability to position an impact surface with the height adjustability of the instant invention compared to conventional instruments that do not have height adjustability and do not accommodate different types of containers and variation in depths, provides an improvement in the number of particles that impact the impact surface and that remain biologically viable. Depending on the variation from optimal separation distance, the improvement may correspond to at least 10%, at least 30% or at least 50% increase in viable counts arising from biological particle impacts compared to conventional instruments.

"Characteristic dimension" refers to a width, diameter, or effective diameter of a flow channel such as an aperture. Effective diameter corresponds to a diameter for a circle having a cross-section area equivalent to the flow channel or aperture.

"Visualization indicator" refers to a component that a user can align by eye so as to position an impact surface at a location that ensures an optimal separation distance is achieved. For example, the visualization indicator may be fixed relative to the aperture exit so as to correspond to an optimal separation distance. An impact surface is connected to the base plate, and due to variations in the geometry of the impact surface, such as impact surface height and/or container configuration, the visualization indicator is used to determine when optimal separation distance is achieved as the user varies the separation distance.

Example 1: Impactors

Figure 1B:
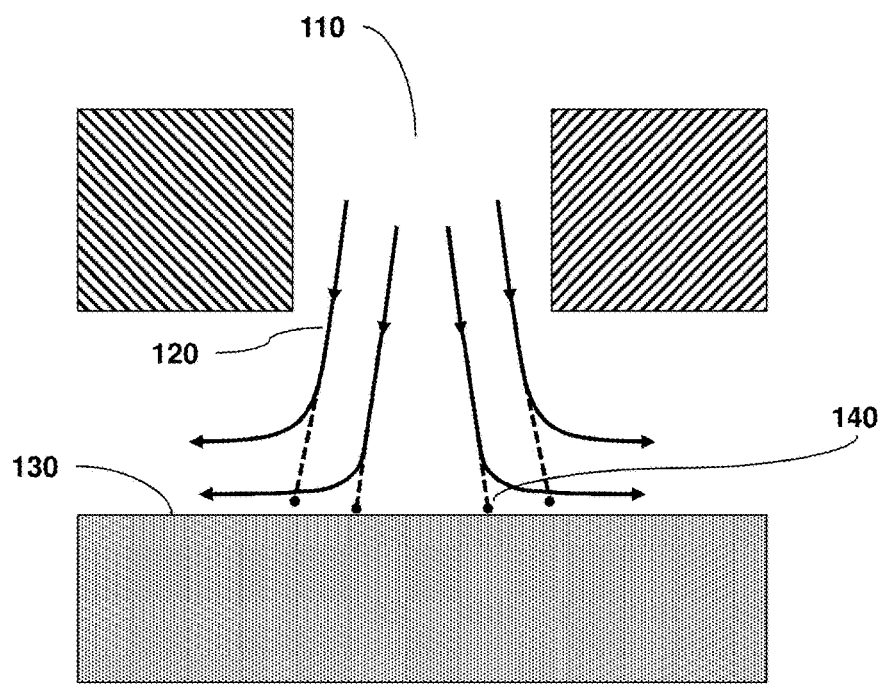

FIG. 1A provides a schematic diagram illustrating the general construction of a particle impactor and FIG. 1B illustrates an expanded view of a particle impactor to further illustrate the operational principal. As shown in these Figures, gas flow is directed through an intake aperture 110 in a sampling head 100 where it is accelerated towards an impact surface 130, which forces the gas to rapidly change direction, following flow paths or streamlines 120 under laminar fluid flow conditions. Due to their momentum, particles 140 entrained in the gas flow are unable to make the rapid change in direction and impact on the impact surface 130. In the embodiment shown in FIG. 1A and FIG. 1B, impact surface 130 is supported by impactor base 150. In embodiments, impact surface 130 comprises the receiving surface of a growth medium, such as agar, provided in a growth medium container or petri dish. Viable biological particles collected on the impact surface, for example, can subsequently be grown and evaluated to provide an analysis of the composition of the fluid flow sampled. For collection of biological particles on the impact surface, control of the separation distance 160, such as a separation distance between the exit 170 of the intake aperture 110 and the impact surface 130, is important. If the distance is too large, for example, the particles may sufficiently follow the fluid path so as to avoid impact with the impact surface. If the distance is too small, however, the particles may impact the impact surface with a force sufficient to render the particles non-viable or otherwise adversely affect the ability of a biological particle to sufficiently reproduce to be visually detected by a user.

Figure 1C:
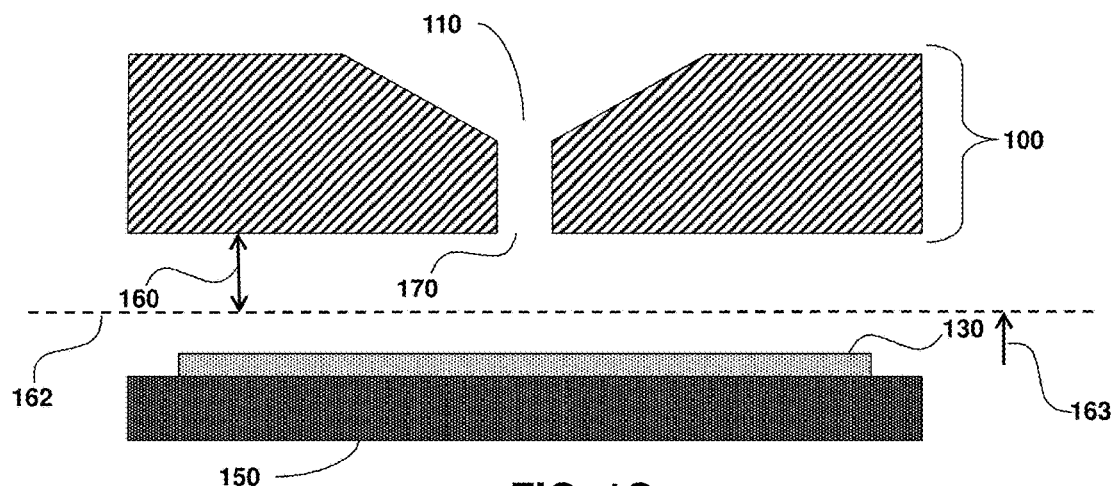
FIGS. 1C and 1D illustrate applications where due to variations in height of the impact surface, the impact surface is not positioned at an optimum separation distance and how the ability to adjust the separation distance in the instant invention can accommodate such variations.
Figure 1D:
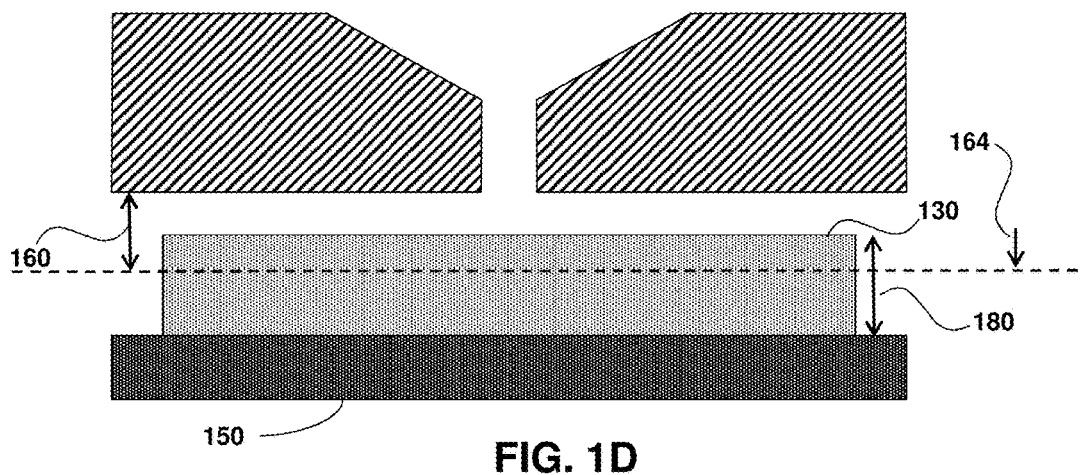
Figure 2:
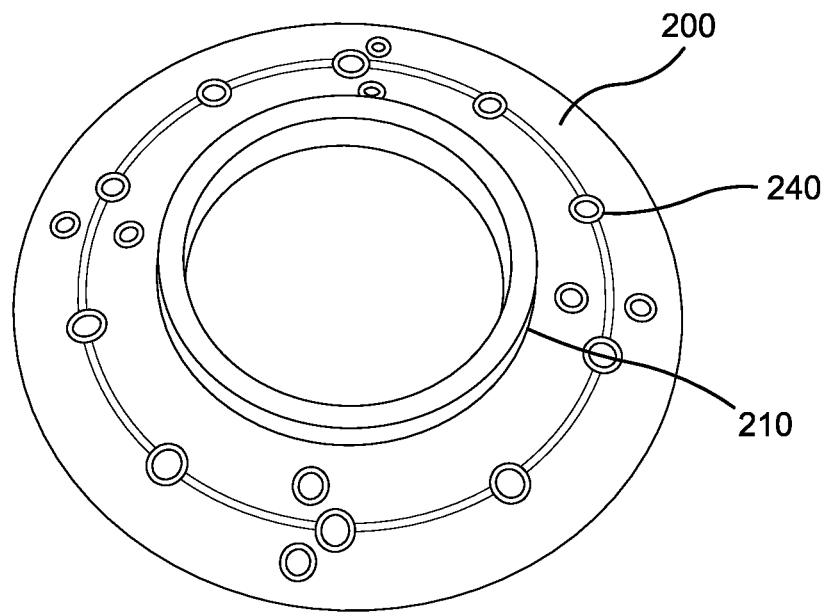
FIG. 2 is an adjustment plate showing a collar or screw top and indents to assist with vertical distance selection

Accordingly, there is a need in the art to ensure an optimum separation distance is achieved independent of, for example, the depth of the impactor surface. Provided herein are methods and devices that accommodate different impactor surface positions, such as for an impactor surface height 180 that may be differ as one impactor surface is swapped out for a different impactor surface (compare FIGS. 1C and 1D). This is particularly relevant for impactor surfaces that correspond to a user-filled growth medium within a container. FIG. 1C-1D schematically illustrate the situations for impact surfaces having relatively small (FIG. 1C) and relatively large (FIG. 1D) depths, resulting in under-impact and artificially low counts (FIG. 1C) and over impacts and potential adverse effects on biological particles (FIG. 1D). The notional dashed line 162 refers to an optimum separation distance corresponding to separation distance 160 of FIG. 1A. The ability of the instant methods and systems to continuously adjust the separation distance ensures that the position of the impact surface 130 is adjusted to align, or substantially align, to the optimum separation distance 162. The direction of movement of impactor base 150 and impact surface 130 is indicated by the direction of arrows 163 and 164 in FIGS. 1C and 1D, respectively Example 2: Height Adjustment of the Agar Media to Position it in an Optimum Position for Physical and Biological Collection Efficiencies When using an active air sampler, where the sampling media is located in relationship to the air inlet impacts, the ability of the device to collect the particles as well as allow them to survive the impaction and grow proper during the incubation cycle depends in part on the separation distance 160 between the impact surface 130 and the exit 170 from the air inlet 110 (see FIGS. 1A-1B)

Samplers on the market today typically use a fixed location where the sampling inlet is a certain distance from the plate support points. Depending upon the media plate used the actual distance to the media can vary from quite close to rather far away (see, e.g., FIGS. 1C-1D). This can lead to either organisms not being impacted on the media and flowing away with the air flow, such as for media that is underfilled or positioned with too high a separation distance 160. Referring to FIG. 1C, this could refer to a impactor surface height 180 that is too low, thereby resulting in a separation distance that is greater than an optimal separation distance 160. Alternatively, for separation distances that are too low, the impact may have too much force causing damage to the organism and adversely affecting growth ability and providing less growth and an accordingly undercount of organisms, such as for media that is overfilled or positioned with insufficient separation distance (FIG. 1D). Referring to FIG. 1D, this could refer to an impactor surface height 180 that is too high, thereby resulting in a separation distance that is less than an optimal separation distance 160.

Figure 3:
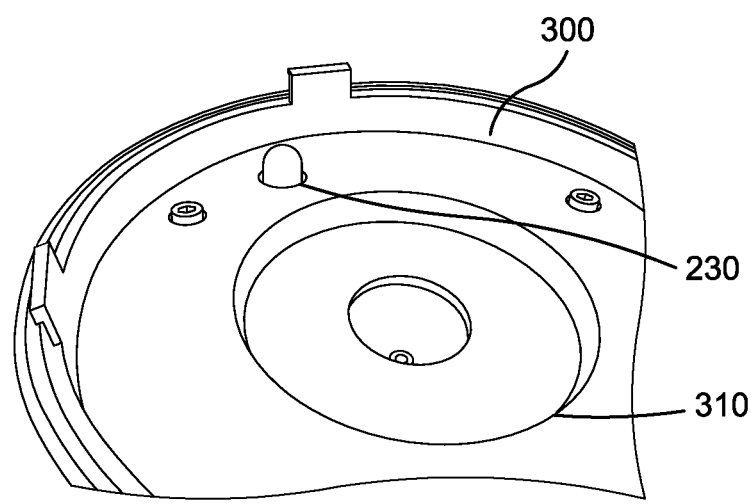
FIG. 3 shows a top portion of a base plate to which the adjustment plate of FIG. 1 connects.
Figure 4:
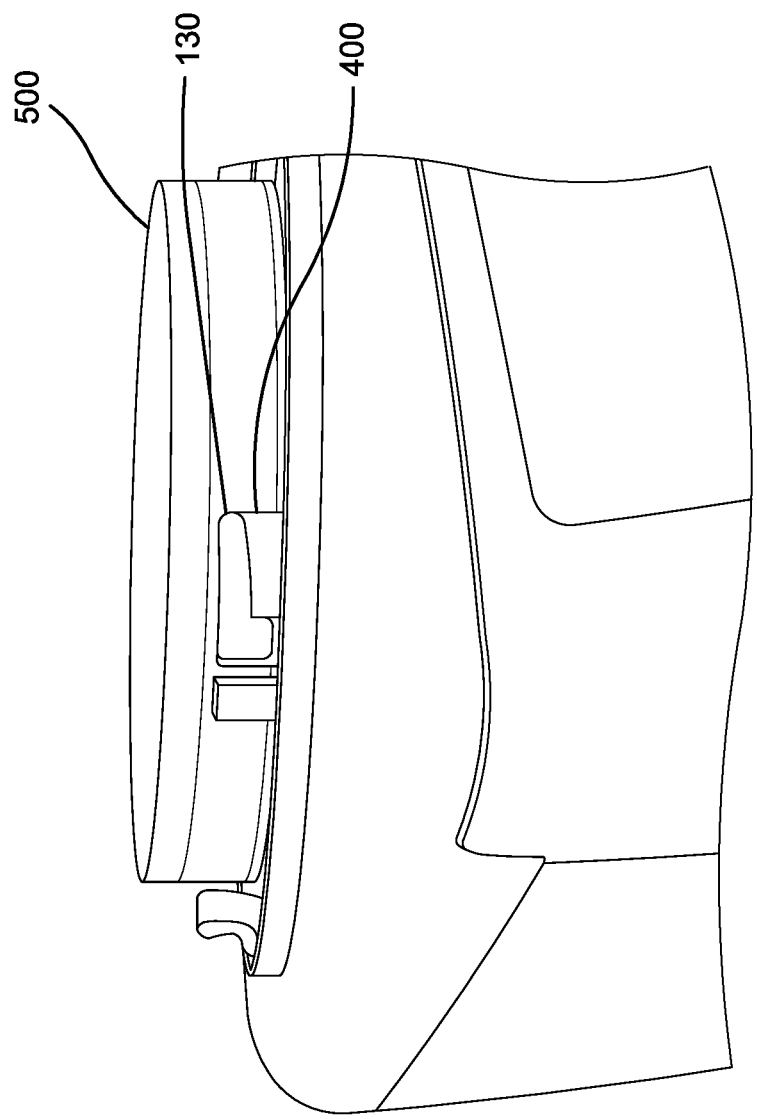
FIG. 4 is a side view of the adjustment plate connected to the base plate and illustrates use of a visualization indicator and an optically transparent container confining an impactor surface to facilitate positioning of the impactor surface at an optimum separation distance.
Figure 5:
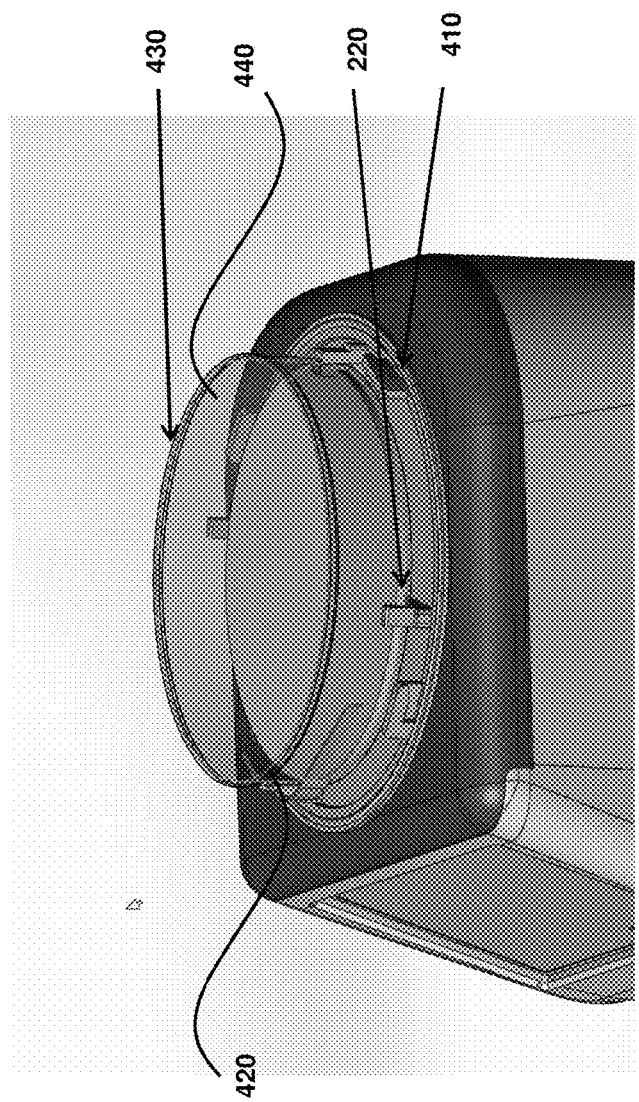
FIG. 5 schematically illustrates an impactor base of an impactor.

Provided herein are air samplers or impactors that incorporate an adjustable plate mechanism to allow for optimum positioning of the media to the air inlets to assure the highest possible collection and growth capabilities (FIGS. 2-7). The adjustment plate 200 (FIG. 2) is positioned based on height of the media in the container so that irrespective of the media height or container type, optimum separation distance is reliably achieved even across multiple different containers. Visual indicators may be used to align with the media height or impact surface. These indicators may be a permanent part of the sampler and may also secure the air sampling head onto the sampling device (FIGS. 4-5). The height of the plate is adjusted by rotating the plate and basically screwing the threaded collar 210 of the adjustment plate 200 into the base plate 300 threaded opening 310 into or out of the device, such as by rotation of adjustment plate (FIG. 2) into and out of threaded opening of the base plate (FIG. 3). The height adjustment plate is held in place with an indent 240 ball assembly 230, also referred herein as separation distance step indicator 220, to prevent the height from changing without interaction to adjust it. This type of arrangement allows for an audible "click" sound for each change in the separation distance for a given rotation of the adjustment plate, such as a indexed separation distance selected from between about 0.05 mm to 0.2 mm separation distance, or about 0.1 mm change in separation distance. FIG. 3 shows the protrusion element 230 as a ball having a spherically-shaped surface for interacting with the indents 240 on the adjustment plate of FIG. 2.

The height of the media is important for optimum collection efficiencies. Without this optimum height and, more specifically, the optimum separation distance, the organisms will either not be collected or could be damaged when they are collected and will not grow into a colony.

By incorporating the height adjustment mechanism into the device there is no need for secondary tools or replacement parts to achieve the optimum height for operation.

Existing products use a fixed height which does not optimize the collection and growth capabilities. Other conventional systems use different pins which require measuring the media plate to be used, calculating the proper height of the media, selecting a specific set of pins to use that will hold the media plate at the optimum height. The pins then need to be placed into the unit using a tool to remove the current pins and replacing them with the proper set. If the media plates change, the same procedure should be repeated for optimum height location or separation distance.

Figure 6:
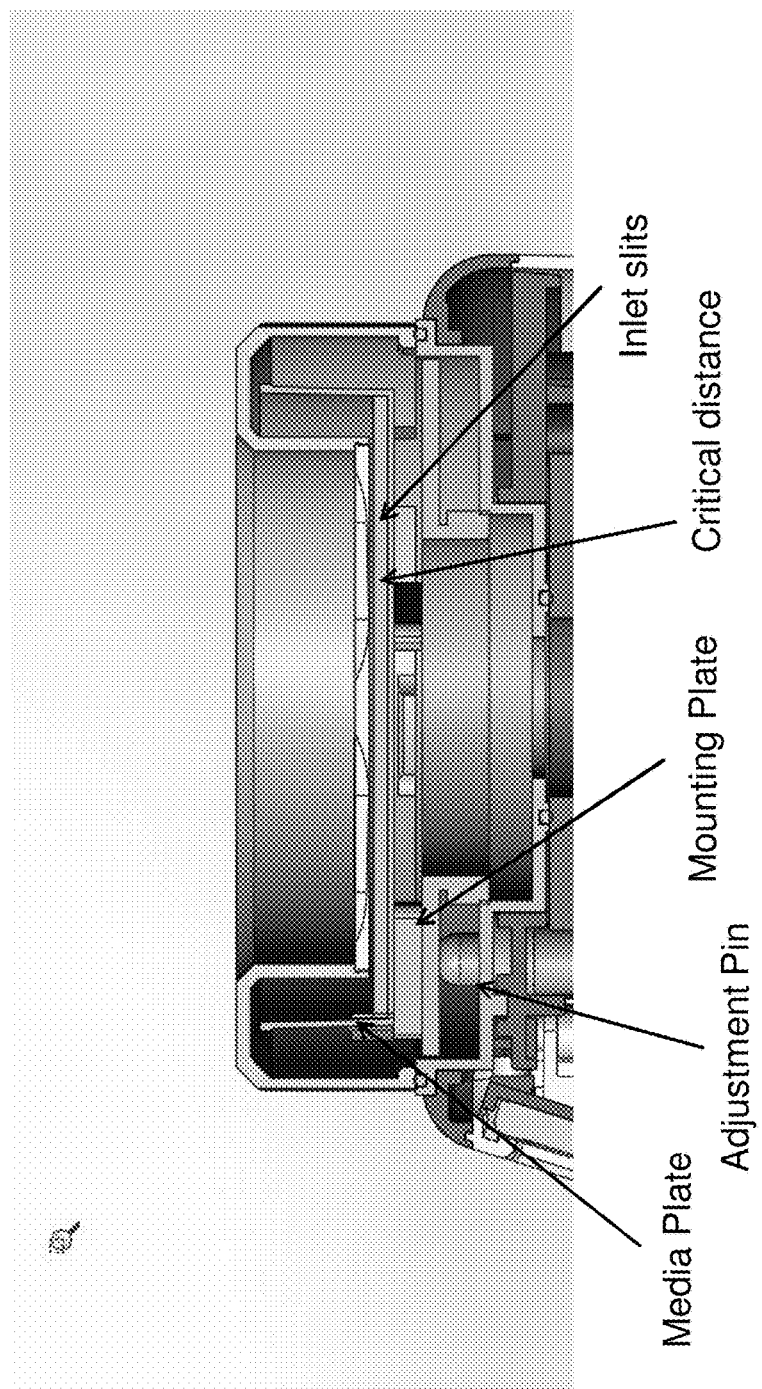
FIG. 6 is a cross-section of an impactor sampling head and impactor base.
Figure 7:
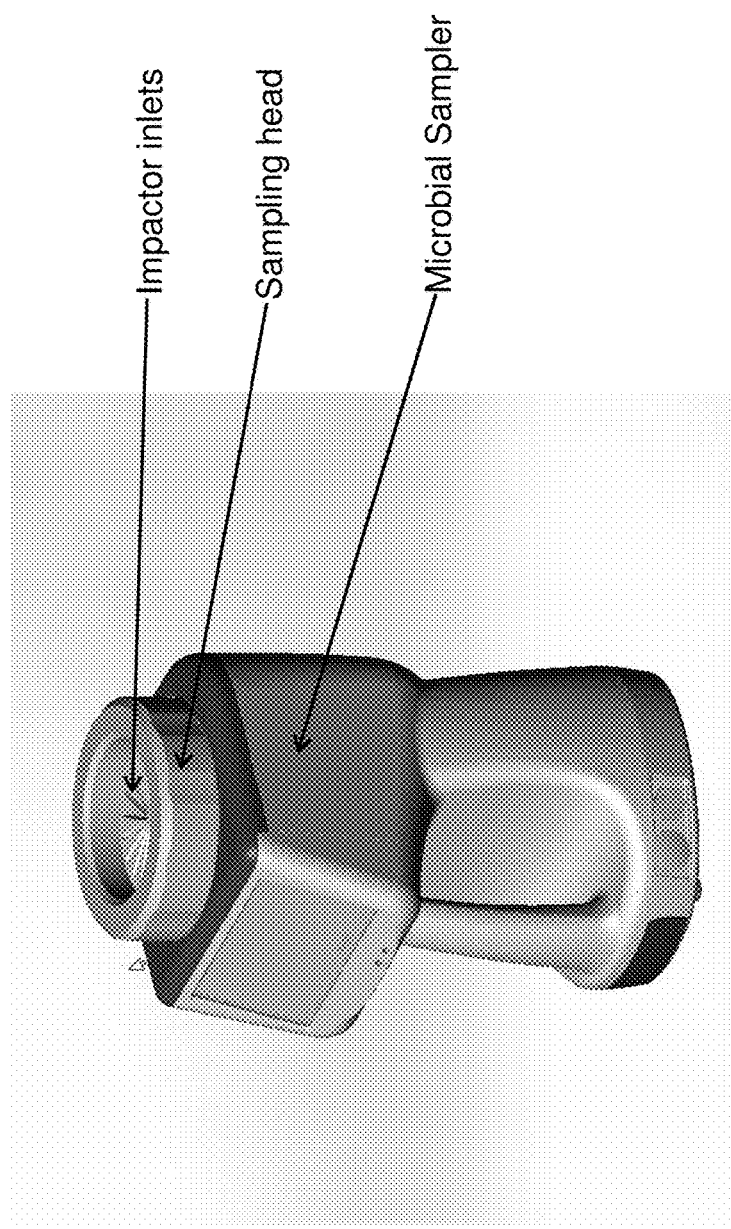
FIG. 7 is a schematic illustration of an impactor.

FIGS. 4-6 show the impactor with a media container 430 or media plate 500 having sidewall 440 affixed thereto, and visualization indictors 400 410 420 (e.g., plate alignment part) for ensuring optimum separation distance is achieved for each media container introduced to the sampler, including impact surface 130. FIG. 7 shows a fully assembled impactor, including the sampling head with intake apertures. In this manner, the impactors of the instant invention can readily and reliably accommodate a wide range of media containers and plates, which may have significantly different impact surface heights.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. An impactor comprising:
a sampling head having at least one intake aperture and an exit;
an impactor base comprising:
an impact surface, wherein the impact surface opposibly faces the sampling head exit and is separated from the exit by a separation distance;
a base plate;
an adjustment plate rotatably connected to the base plate, wherein the adjustment plate rotates relative to the base plate to provide a continuously adjustable separation distance between a minimum separation distance and a maximum separation distance; and
a separation distance step indicator operably connected to the base plate or the adjustment plate to indicate a change in the separation distance for a given rotation of the adjustment plate;
wherein the separation distance step indicator comprises a protrusion element connected to the base plate and a plurality of indents formed on a surface of the adjustment plate, wherein the protrusion element is configured to mate with each of the plurality of indents;
wherein the plurality of indents are equally spaced apart from each other by an indent separation distance, wherein a change in mating of the protrusion element from a first indent to an adjacent indent corresponds to a change in the separation distance.

2. The impactor of claim 1, wherein the adjustment plate comprises a threaded collar and the base plate comprises a threaded opening, wherein the threaded collar and threaded opening form paired internal-external threads to provide the continuously adjustable separation distance by rotation of the threaded collar relative to the threaded opening.

3. The impactor of claim 1, wherein the separation distance corresponds to an optimal separation distance.

4. The impactor of claim 3, wherein the optimal separation distance is about twice a characteristic dimension of an opening size of the sampling head exit.

5. The impactor of claim 3, wherein the optimal separation distance is greater than or equal to 0.1 mm and less than or equal to 1.5 mm; or is greater than or equal to a width of the sampling head exit and less than or equal to about three times the width of the sampling head exit.

6. The impactor of claim 1, wherein:
the minimum separation is selected from a range that is greater than 0 and less than 0.2 mm; and
the maximum separation distance is greater than the minimum separation distance and is selected from a range that is greater than 0.1 mm and less than or equal to 5 mm.

7. The impactor of claim 1, wherein the indent separation distance is selected to provide the change in the separation distance that is greater than or equal to 0.05 mm and less than or equal to 0.5 mm.

8. The impactor of claim 7, wherein the adjustment plate comprises a threaded collar and the base plate comprises a threaded opening;
wherein the threaded collar and threaded opening form paired internal-external threads to provide the continuously adjustable separation distance by rotation of the threaded collar relative to the threaded opening; and
wherein the plurality of indents are concentrically positioned around the collar so that rotation of the adjustable plate from a first indent to a spatially adjacent second indent corresponds to the change in separation distance.

9. The impactor of claim 1, wherein the protrusion element and indents are configured to provide an audible mechanically-generated sound when a protrusion element mates with an indent.

10. The impactor of claim 9, wherein the protrusion element comprises a spherical shaped outer surface and the indent is shaped to receive at least a portion of the spherical shaped outer surface.

11. The impactor of claim 1, further comprising one or more visualization indicators connected to the impactor base for positioning the impact surface at a separation distance corresponding to a desired separation distance.

12. The impactor of claim 11, comprising a first visualization indicator and a second visualization indicator, wherein the first and second visualization indicators are opposibly positioned with respect to each other, wherein the impact surface is positioned between the first and the second visualization indicators.

13. The impactor of claim 11, further comprising a container in which the impact surface is positioned, wherein the container has a side wall that constrains the impact surface and at least a portion of the side wall is optically transparent for visual alignment of the visualization indicator with a top surface of the impact surface.

14. The impactor of claim 11, wherein the impact surface comprises a top surface of a growth medium, and the top surface of the growth medium is aligned with the plurality of visualization indicators.

15. The impactor of claim 14, wherein a plurality of visualization indicators secure the sampling head to the impactor base.

16. The impactor of claim 14, wherein the impact surface is constrained within a container having a sidewall top and the impact surface top surface is substantially coincident with the container sidewall top.

17. The impactor of claim 1, wherein the impact surface comprises a top surface of a biological growth medium.

18. The impactor of claim 17, wherein the biological growth medium comprises agar.

19. The impactor of claim 17, wherein the biological growth medium is confined within a growth media container.

20. The impactor of claim 19:
wherein the adjustment plate comprises a threaded collar and the base plate comprises a threaded opening and rotation of the threaded collar relative to the threaded opening provides the continuously adjustable separation distance,
wherein the threaded collar is connected to a bottom surface of the adjustment plate, and the growth media container is supported by a top surface of the rotatable adjustment plate.

21. The impactor of claim 20, wherein the growth media container comprises a cell-culture dish.

22. The impactor of claim 20, wherein the impactor base is adjusted to achieve an optimal separation distance that accommodates container-to-container variation in a growth medium depth of the biological growth medium confined within the growth media container.

23. The impactor of claim 22, wherein the growth media container in the impactor is removable and replaceable.

24. The impactor of claim 23, wherein a depth of the growth medium within the growth media container is different for a replacement growth media container, and the continuously adjustable separation distance provides an optimal separation distance for the replacement growth media container.

25. The impactor of claim 1, wherein the sampling head comprises a plurality of openings, each opening having an inlet and an outlet.

26. A method for detecting biological particles with an impactor comprising the steps of:
providing a biological growth medium in a media container, the biological growth medium having a top surface that corresponds to an impact surface;
positioning the media container on a top surface of an adjustment plate, wherein the adjustment plate has a threaded collar connected to a bottom surface of the adjustment plate;
rotatably connecting the adjustment plate to a threaded opening on an impactor base;
rotating the adjustment plate relative to the impactor base, thereby continuously adjusting a separation distance between the impact surface and an exit of a sampling head of the impactor by an indexed separation distance;
indicating to a user an adjusted separation distance corresponding to the indexed separation distance, wherein the indicating comprises a mechanically generated sound generated by a protrusion element moving into an indent with a rotation that provides a change in separation distance corresponding to the indexed separation distance;
wherein a plurality of indents are provided on a surface of the adjustment plate; wherein the protrusion element is configured to mate with each of the plurality of indents; and wherein the plurality of indents are equally spaced apart from each other by an indent separation distance, wherein a change in mating of the protrusion element from a first indent to an adjacent indent corresponds to a change in the separation distance; and
flowing a sample fluid through the exit of the sampling head, wherein the optimal separation distance provides impaction of biological particles suspended in the sample fluid, thereby detecting the biological particles.

27. An impactor comprising:
a sampling head having at least one intake aperture and an exit;
an impactor base comprising:
an impact surface, wherein the impact surface opposibly faces the sampling head exit and is separated from the exit by a separation distance;
a base plate;
an adjustment plate rotatably connected to the base plate, wherein the adjustment plate rotates relative to the base plate to provide a continuously adjustable separation distance between a minimum separation distance and a maximum separation distance; and
a separation distance step indicator operably connected to the base plate or the adjustment plate to indicate a change in the separation distance for a given rotation of the adjustment plate;
one or more visualization indicators connected to the impactor base for positioning the impact surface at a separation distance corresponding to a desired separation distance;
wherein the impact surface comprises a top surface of a growth medium, and the top surface of the growth medium is aligned with the plurality of visualization indicators; and
wherein a plurality of visualization indicators secure the sampling head to the impactor base.

* * * * *